United States Patent [19]

Cavazza

[11] Patent Number: 5,192,805
[45] Date of Patent: Mar. 9, 1993

[54] USE OF ACETYL L-CARNITINE IN THE THERAPEUTIC TREATMENT OF COMA

[75] Inventor: Claudio Cavazza, Rome, Italy

[73] Assignee: Sigma-Tau Industrie Farmaceutiche Riunite S.p.A., Rome, Italy

[21] Appl. No.: 816,224

[22] Filed: Jan. 3, 1992

[30] Foreign Application Priority Data

Jan. 4, 1991 [IT] Italy ................................... 91 000002

[51] Int. Cl.$^5$ ............................................ A61K 31/205
[52] U.S. Cl. .................................................... 514/556
[58] Field of Search .......................................... 514/556

[56] References Cited

U.S. PATENT DOCUMENTS 4,464,393 8/1984 Cavazza .............................. 514/556
4,751,242 6/1988 Calvani et al. ...................... 514/556

Primary Examiner—Frederick E. Waddell
Assistant Examiner—K. Weddington
Attorney, Agent, or Firm—Oblon, Spivak, McClelland, Maier & Neustadt

[57] ABSTRACT

The use is described of acetyl L-carnitine and some of its pharmacologically acceptable salts in the therapeutic treatment of coma. 2000-4000 mg/day of acetyl L-carnitine or an equivalent quantity of one of its pharmacologically acceptable salts is administered, preferably by the parenteral route.

4 Claims, No Drawings

USE OF ACETYL L-CARNITINE IN THE THERAPEUTIC TREATMENT OF COMA

This invention concerns a new therapeutic application of acetyl L-carnitine and some of its pharmacologically acceptable salts in the therapeutic treatment of coma, particularly of traumatic coma.

Earlier therapeutic uses of acetyl carnitine are already known. For example, in U.S. Pat. No. 4,194,006 the use is described of acetyl carnitine in the therapeutic treatment of myocardial ischemia and arrhythmias. In U.S. Pat. No. 4,343,816 the use is described of acetyl carnitine in the therapeutic treatment of functional peripheral arterial vasculopathies such for example as Raynaud's disease and acrocyanosis. In U.S. Pat. No. 4,346,107 is described the therapeutic utility of acetyl carnitine in the treatment of patients affected by altered cerebral metabolism which appears for example in senile and pre-senile dementia and in Alzheimer's disease. However there is no correlation between the known therapeutic applications of acetyl L-carnitine and the application which forms the subject of this invention.

The term coma should be limited to the conditions which are consistent with the definition of Plum (1972) who considers it "unrousable unresponsiveness". In practice, in reanimation centres and intensive care centres where it is treated, the term coma is used to indicate a wide range of clinical conditions which have in common only the alteration of consciousness.

Coma is a condition during which the individual appears to sleep, but in reality is incapable of perceiving or adequately responding to either external or internal stimuli. It is the most serious form of sensory impairment which affects man.

Some forms of coma have behavioural characteristics sufficiently similar to be considered until a few years ago as all caused by a reduction of the impulses originating in the reticular activating system which project to the hemispheres.

It is opportune to distinguish between the following states of coma:

Akinetic mutism is synonymous with coma vigil. It presents a condition of silent immobility and the absence of mental and motor activity. The individual keeps his eyes closed, is deprived of speech, has approximate sphincteric continence and responds with rudimentary movements to nociceptive stimulus.

Apallic syndrome is a condition which accompanies diffuse bilateral degeneration of the cerebral cortex as a consequence of anoxia, cranial trauma, and encephalitis. Cortical function is absent while that of the brain stem is retained.

The "locked-In" syndrome is present in cases of quadraplegia and paralysis of the lower cranial nerves caused by selective denervation of the super-nuclear neurons, while consciousness is retained. The individual is able to blink and move his eyes vertically in such a way that some have learned to communicate by means of these signs in the manner of Morse code.

In the vegative state (a sub-acute or chronic condition following anoxic-ischaemic coma, with a return to the state of wakefulness and total loss of the cognitive function), there is opening of the eyes in response to verbal stimulation, presence of the wakefulness/sleep cycle, normal arterial pressure, spontaneous pulmonary ventilation, and the absence of motor responses. This situation may persist even for years.

In "cerebral death" it is customary to distinguish between "brain death" and "cerebral death": In the former case, the neuronal content of the cranial cavity has been destroyed, while in the latter there is the destruction only of the hemispheres but not of the brain stem and of the cerebellum. In every case the damage is however irreversible. To avoid confusion, the term "cerebral death" has commonly been substituted by "irreversible coma".

Comas can also be classified according to the originating cause.

Barbiturate coma, caused by acute barbiturate intoxication, is even today very frequent.

The causes are for the most part associated with suicide attempts.

One distinguishes two types of poisoning, those by slow-acting barbiturates and those by fast-acting barbiturates.

The former cause prolonged comas that are not severe, with various complications: in particular superinfections of the respiratory tract.

Endocrine coma manifests with a modification in the state of wakefulness, of greater or lesser severity, depending on alterations in the hormonal activity essential for the homeostasis of the organism.

One distinguishes according to the alterations present between the following comatose states: dehydrational coma (diabetes insipidus), hypo-pituitary coma; myxoedematous coma; thyrotoxic coma; adrenocortical hypofunction; hypercalcamic coma; hepatic coma; uraemic coma.

Cerebral oedema may occur in the course of varied pathological processes: cerebro-vascular lesions, neoplasmas, cranial traumas, and infective diseases.

Whether circumscribed or diffuse, cerebral oedema, being the most common cause of raised intracranial pressure, causes local damage (compression, vascular disorders) and remote damage (cerebral hernias), leading in the patient, according to the localisation of the damage, to respiratory or circulatory disorders, and even to a comatose state.

At present there are no medications in commercial use which have an effectual arousing effect, this term being used to indicate a medication which has the ability to re-establish organic homeostasis to such an extent as to promote the revival of the level of consciousness. For example, citicholine, which although seeming to act at the cerebral level and to improve the circulation by increasing the blood flow and the consumption and utilisation of oxygen, and piracetam, which seems to induce an increase in the energy potential of the nerve cells by means of an increased supply of ATP, accelerating post-hypoxic and post-traumatic recuperation, are ineffective agents for arousal in the treatment of traumatic coma.

It has now surprisingly been found that the use of acetyl L-carnitine and some of its pharmacologically acceptable salts is effective in the therapeutic treatment of coma, particularly of traumatic coma.

The loss of acute consciousness which follows cranial trauma is one of the main causes of the comatose state.

Because of the physiological implications of coma, it follows that when a super-tentorial lesion affects consciousness, intensive medical treatment should guarantee adequate transportation of substrates and oxygen to the cerebrum, that is to say, to ensure a sufficient cerebral perfusion.

A determining factor in the perfusion is the intracranial pressure (ICP) since the cerebral perfusion pressure (CPP) depends on the difference between the mean arterial pressure (MAP) and the ICP.

The intracranial pressure reflects at every moment the resultant of the static and dynamic forces which act on the intracranial contents.

The cranium and the ventricular system and their contents constitute a semi-rigid compartment which communicates with the exterior by means of the cardiovascular system.

In fact when one observes, as in the case of a cranial trauma, that the arterial pressure is falling or that the intracranial pressure is increasing, the pressure of cerebral perfusion decreases proportionally.

Therefore every agent capable of modifying the cerebral blood flow can induce positive results in perfusion but at the same time determines, with the increase in the cephalic blood content, the intracranial pressure (ICP). This increase in traumatised cranial contents could have extremely dangerous results because of the risk of irreversible cerebral damage.

Acetyl L-carnitine is able to increase the cerebral blood flow (CBF) as has in fact been demonstrated by studies conducted in acute cases after intravenous administration. Acetyl L-carnitine has in fact lead to significant increases in the CBF measured by means of SPECT (Single-Photon Emission Computed Tomography): see Battistin et al., European Neurology, 1989; 29; 261–265; and Postigllone et al, Int. J. Clin. Pharm. Res. X 129–132; 1990. The results of these and other studies constitute a strong argument against the administration of acetyl L-carnitine in patients with traumatic coma, according to what has been previously disclosed.

The applicant has instead now shown that the administration of acetyl L-carnitine to patients with cranial trauma not only does not cause negative effects, but that the state of wakefulness which had previously been altered is revived. In other words, it has been found that acetyl L-carnitine is effectually endowed with that "arousing effect" which the medications currently used commercially do not have.

A multicentre placebo-controlled double-bind study has been carried out on 140 patients in post-traumatic coma.

The patients had coma of type II and III with a G.C.S. (Glasgow Coma Scale) between 3 and 12.

At the start of the treatment the two groups (Active and Placebo) were homogeneous, as set out in Table 1.

TABLE 1

|  | ALC | PLACEBO |
|---|---|---|
| AGE | 37.5 ± 22.24 | 39.24 ± 20.08 |
| G.C.S. | 6.37 ± 2.54 | 6.38 ± 2.44 |
| PERIOD FROM ADMISSION TO TREATMENT (DAYS) | 4.65 ± 4.5 | 4.89 ± 5.65 |

All the subjects were treated with 60 mg/kg of ALC or Placebo according to a randomisation schedule.

Statistical analysis carried out by means of the Wilcoxon test showed significance with $p < 0.01$, showing more rapid awakening for the group treated with ALC (Table 2).

TABLE 2

|  | ALC | PLACEBO |
|---|---|---|
| DURATION OF THE COMA (DAYS) | 5.91 ± 3.87 | 9.06 ± 5.63 |

This invention accordingly contemplates the use of acetyl L-carnitine and some of its pharmacologically acceptable salts as a medication with an arousing effect to produce a pharmacological composition for the therapeutic treatment of coma, in particular of traumatic coma. In practice, it is preferable to administer approximately from 2000 to 4000 mg per day of acetyl L-carnitine or an equivalent quantity of one of its pharmacologically acceptable salts.

The most suitable pharmacological compositions for parenteral administration are some of the compositions which, in the form of a single dose, comprise from about 500 to about 1000 mg of acetyl L-carnitine or of an equivalent quantity of one of its pharmacologically acceptable salts and an excipient that is pharmacologically acceptable and compatible with the active constituent. Examples of suitable compositions in the form of a single dose are described in for example U.S. Pat. No. 4,464,393.

What is claimed is:

1. A therapeutical method for the treatment of coma which comprises parenterally administering to a subject in a coma an amount of acetyl L-carnitine or a pharmacologically acceptable salt thereof effective for arousing the patient from coma.

2. The method of claim 1, which comprises administering to said subject in a coma from 2,000 to 4,000 mg/day of acetyl L-carnitine or an equivalent amount of a pharmacologically acceptable salts thereof.

3. The method of claim 1, wherein said coma is a traumatic coma.

4. The method of claim 2, which comprises administering to said subject in a coma single dosages comprising from about 500 to about 1000 mg of acetyl L-carnitine or an equivalent amount of a pharmacologically acceptable salt thereof.

* * * * *